United States Patent
Osio Sancho

(10) Patent No.: US 9,566,317 B2
(45) Date of Patent: *Feb. 14, 2017

(54) TREATMENT OF OPHTHALMIC CONDITIONS

(71) Applicant: Osio Corporation, Coronado, CA (US)

(72) Inventor: Alberto Osio Sancho, Mexico, D.F. (MX)

(73) Assignee: Osio Corporation, Coronado, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,246

(22) Filed: Jan. 22, 2016

(65) Prior Publication Data

US 2016/0367647 A1    Dec. 22, 2016

Related U.S. Application Data

(60) Continuation of application No. 14/532,851, filed on Nov. 4, 2014, now Pat. No. 9,241,980, which is a division of application No. 14/223,130, filed on Mar. 24, 2014, now Pat. No. 8,877,228, which is a continuation of application No. 13/932,842, filed on Jul. 1, 2013, now Pat. No. 8,679,521, which is a continuation of application No. 10/582,728, filed as application No. PCT/US2004/042660 on Dec. 17, 2004, now Pat. No. 8,475,831.

(30) Foreign Application Priority Data

Dec. 19, 2003 (MX) ...................... 011987

(51) Int. Cl.

| A61F 2/00 | (2006.01) |
|---|---|
| A61K 9/00 | (2006.01) |
| A61K 38/46 | (2006.01) |
| G02C 7/04 | (2006.01) |
| A61K 38/48 | (2006.01) |
| A61K 38/47 | (2006.01) |

(52) U.S. Cl.
CPC .......... *A61K 38/4886* (2013.01); *A61K 38/47* (2013.01)

(58) Field of Classification Search
None
See application file for complete search history.

(56) References Cited

U.S. PATENT DOCUMENTS

| 3,945,889 A | 3/1976 | Mima et al. |
|---|---|---|
| 3,957,049 A | 5/1976 | Neefe |
| 4,258,134 A | 3/1981 | Yoshida et al. |
| 4,418,991 A | 12/1983 | Breger |
| 4,484,922 A | 11/1984 | Rosenwald |
| 4,540,417 A | 9/1985 | Poler |
| 4,571,039 A | 2/1986 | Poler |
| 4,592,752 A | 6/1986 | Neefe |
| 4,713,446 A | 12/1987 | DeVore et al. |
| 4,759,746 A | 7/1988 | Straus |
| 4,820,016 A | 4/1989 | Cohen et al. |
| 4,851,513 A | 7/1989 | DeVore et al. |
| 4,881,543 A | 11/1989 | Trembly et al. |
| 4,897,349 A | 1/1990 | Swann et al. |
| 4,904,594 A | 2/1990 | Karistam et al. |
| 4,952,045 A | 8/1990 | Stoyan |
| 4,969,912 A | 11/1990 | Kelman et al. |
| 5,061,627 A | 10/1991 | Olsen et al. |
| 5,144,630 A | 9/1992 | Lin |
| 5,163,956 A | 11/1992 | Liu et al. |
| 5,196,027 A | 3/1993 | Thompson et al. |
| 5,201,764 A | 4/1993 | Kelman et al. |
| 5,270,051 A | 12/1993 | Harris |
| 5,316,926 A | 5/1994 | Brown et al. |
| 5,354,331 A | 10/1994 | Schachar |
| 5,465,737 A | 11/1995 | Schachar |
| 5,484,432 A | 1/1996 | Sand |
| 5,489,299 A | 2/1996 | Schachar |

(Continued)

FOREIGN PATENT DOCUMENTS

| EP | 0 193 330 A2 | 9/1986 |
|---|---|---|
| EP | 0 459 148 A2 | 12/1991 |

(Continued)

OTHER PUBLICATIONS

Austrian Search Report, mailed Jul. 2, 2014, in connection with Application No. UAE/P/452/2006.
International Preliminary Report on Patentability for PCT/US2004/042660, mailed Jun. 29, 2006.
International Search Report and Written Opinion for International Application Serial No. PCT/US04/042660, mailed Aug. 4, 2005.
International Preliminary Report on Patentability, mailed Feb. 19, 2015, in connection with Application No. PCT/US2013/054425.
International Search Report and Written Opinion for International Application Serial No. PCT/US2013/054425, dated Oct. 2, 2013.
Supplementary European Search Report for EP 04814801.9, mailed Feb. 27, 2012.

(Continued)

*Primary Examiner* — Jeffrey T Palenik
(74) *Attorney, Agent, or Firm* — Wolf, Greenfield & Sacks, P.C.

(57) ABSTRACT

Ophthalmic conditions such as presbyopia, myopia, and astigmatism can be corrected by the use of a molding contact lens in combination with a pharmaceutical composition suitable for delivery to the eye. The molding contact lenses are preferably commercially available and are not specifically designed for orthokeratology. The agents in the pharmaceutical compositions such as hyaluronase allow the cornea of the eye to be molded in order to correct the refractive error of the eye. The contact lenses and the pharmaceutical composition induce a change in the radius of curvature of the anterior surface of the cornea, thereby correcting the refractive error of the eye. One advantage of the inventive technique is that the patient with his or her own individual visual needs guides the treatment until the patient near and far visual needs are met. The present invention also provides for kits, which contain molding contact lenses, pharmaceutical composition suitable for delivery to the eye, and instructions, useful in the inventive system.

20 Claims, 8 Drawing Sheets

(56) References Cited

U.S. PATENT DOCUMENTS

| | | |
|---|---|---|
| 5,492,135 A | 2/1996 | DeVore et al. |
| 5,496,726 A | 3/1996 | Park et al. |
| 5,518,732 A | 5/1996 | Nigam |
| 5,520,679 A | 5/1996 | Lin |
| 5,529,076 A | 6/1996 | Schachar |
| 5,580,570 A | 12/1996 | Robertson et al. |
| 5,593,877 A | 1/1997 | King |
| 5,626,865 A | 5/1997 | Harris et al. |
| 5,695,509 A | 12/1997 | El Hage |
| 5,722,952 A | 3/1998 | Schachar |
| 5,747,027 A | 5/1998 | Stern et al. |
| 5,756,552 A | 5/1998 | Takeuchi et al. |
| 5,779,696 A | 7/1998 | Berry et al. |
| 5,788,957 A | 8/1998 | Harris |
| 5,792,103 A | 8/1998 | Schwartz et al. |
| 5,815,237 A | 9/1998 | Vayntraub |
| 5,827,721 A | 10/1998 | Stern et al. |
| 5,866,120 A | 2/1999 | Karageozian et al. |
| 5,894,002 A | 4/1999 | Boneberger et al. |
| 5,963,297 A | 10/1999 | Reim |
| 6,010,219 A | 1/2000 | Stovan |
| 6,037,144 A | 3/2000 | Fedorov et al. |
| 6,039,943 A | 3/2000 | Karageozian et al. |
| 6,123,938 A | 9/2000 | Stern et al. |
| 6,132,735 A | 10/2000 | Harris et al. |
| 6,161,544 A | 12/2000 | DeVore et al. |
| 6,258,082 B1 | 7/2001 | Lin |
| 6,261,545 B1 | 7/2001 | Okamoto |
| 6,263,879 B1 | 7/2001 | Lin |
| RE37,336 E | 8/2001 | Weigel et al. |
| 6,296,847 B1 | 10/2001 | Gokcen et al. |
| 6,335,006 B1 | 1/2002 | Miller |
| 6,426,208 B1 | 7/2002 | Kakkis et al. |
| 6,537,545 B1 | 3/2003 | Karageozian et al. |
| 6,543,897 B1 | 4/2003 | Tung |
| 6,551,590 B2 | 4/2003 | Karageozian et al. |
| 6,569,661 B1 | 5/2003 | Qin et al. |
| 6,585,971 B1 | 7/2003 | Kakkis |
| 6,595,986 B2 | 7/2003 | Almeida |
| 6,610,292 B2 | 8/2003 | Karageozian et al. |
| 6,652,095 B2 | 11/2003 | Tung |
| 6,710,051 B1 | 3/2004 | Trier |
| 6,733,124 B2 | 5/2004 | Miyamura |
| 6,737,075 B2 | 5/2004 | Karageozian |
| 6,773,699 B1 | 8/2004 | Soltz et al. |
| 6,780,840 B1 | 8/2004 | DeVore et al. |
| 6,858,206 B2 | 2/2005 | Kakkis |
| 6,875,427 B1 | 4/2005 | DeVore et al. |
| 6,902,548 B1 | 6/2005 | Schuler et al. |
| 6,939,364 B1 | 9/2005 | Soltz et al. |
| 6,939,542 B2 | 9/2005 | Karageozian et al. |
| 6,946,440 B1 | 9/2005 | DeWoolfson et al. |
| 7,070,275 B2 | 7/2006 | Tung |
| 7,346,416 B2 | 3/2008 | Wadding et al. |
| 7,559,649 B2 | 7/2009 | Cotie et al. |
| 8,475,831 B2 | 7/2013 | Sancho |
| 8,679,521 B2 | 3/2014 | Sancho |
| 8,877,228 B2 | 11/2014 | Sancho |
| 9,086,580 B2 | 7/2015 | Grant et al. |
| 9,241,980 B2 | 1/2016 | Osio Sancho |
| 2002/0164316 A1 | 11/2002 | Karageozian et al. |
| 2002/0185139 A1 | 12/2002 | Soll |
| 2003/0139737 A1 | 7/2003 | Lin |
| 2003/0170224 A1 | 9/2003 | Karageozian et al. |
| 2003/0175259 A1 | 9/2003 | Karageozian et al. |
| 2005/0080484 A1 | 4/2005 | Marmo et al. |
| 2005/0256065 A1 | 11/2005 | Harris et al. |
| 2008/0024717 A1 | 1/2008 | Kim |
| 2012/0320334 A1 | 12/2012 | Ho et al. |
| 2014/0043588 A1 | 2/2014 | Grant et al. |
| 2015/0216952 A1 | 8/2015 | Sancho |

FOREIGN PATENT DOCUMENTS

| | | |
|---|---|---|
| EP | 0 608 341 A1 | 8/1994 |
| EP | 1 159 941 A2 | 12/2001 |
| JP | 7-500267 A | 1/1995 |
| JP | 8-67617 A | 3/1996 |
| MX | PA05000125 A | 6/2006 |
| RU | 2166785 C1 | 5/2001 |
| WO | WO 91/16070 A1 | 10/1991 |
| WO | WO 93/07840 A1 | 4/1993 |
| WO | WO 94/02084 A1 | 2/1994 |
| WO | WO 97/18835 A1 | 5/1997 |
| WO | WO 98/52090 A1 | 11/1998 |
| WO | WO 99/40933 A1 | 8/1999 |
| WO | WO 99/45869 A1 | 9/1999 |
| WO | WO 00/30578 A1 | 6/2000 |
| WO | WO 00/66139 A2 | 11/2000 |
| WO | WO 01/34176 A1 | 5/2001 |
| WO | WO 2004/015479 A2 | 2/2004 |
| WO | WO 2005/062818 A2 | 7/2005 |

OTHER PUBLICATIONS

Hesse, Using enzymes in the posterior eye segment. Current status and future possibilities. Ophthalmologe. Dec. 2001;98(12):1176-80. Review.

Humphrey, International standard for hyaluronidase. Bull World Health Organ. 1957;16(2):291-4.

Lui et al., Orthokeratology in low myopia. Part 1: efficacy and predictability. Cont Lens Anterior Eye. 2000;23(3):77-89.

Okada et al., Degradation of type IX collagen by matrix metalloproteinase 3 (stromelysin) from human rheumatoid synovial cells. FEBS Lett. Feb. 27, 1989;244(2):473-6.

Swarbrick et al., Orthokeratology review and update. Clin Exp Optom. May 2006;89(3):124-43.

TREATMENT OF OPHTHALMIC CONDITIONS

PRIORITY INFORMATION

The present application is a continuation of and claims priority under 35 U.S.C. §120 to U.S. patent application Ser. No. 14/532,851, filed Nov. 4, 2014, which is a divisional of and claims priority under 35 U.S.C. §120 to U.S. patent application Ser. No. 14/223,130, filed Mar. 24, 2014, now issued U.S. Pat. No. 8,877,228, which is a continuation of and claims priority under 35 U.S.C. §120 to U.S. patent application Ser. No. 13/932,842, filed Jul. 1, 2013, now issued as U.S. Pat. No. 8,679,521, which is a continuation of and claims priority under 35 U.S.C. §120 to U.S. patent application Ser. No. 10/582,728, filed Jun. 14, 2006, now issued U.S. Pat. No. 8,475,831, which is a national stage filing under 35 U.S.C. §371 of international PCT application, PCT/US2004/042660, filed Dec. 17, 2004, which claims priority under 35 U.S.C. §119(a) to Mexican patent application, No. PA/a/2003/011987, filed Dec. 19, 2003, entitled "MÉTODO PARA EL TRATAMIENTO DE LA PRESBICIA INDUCIENDO CAMBIOS EN EL PODER Y FISIOLOGIA CORNEAL," each of which is incorporated herein by reference.

FIELD OF THE INVENTION

The present invention provides a system for treating presbyopia, myopia, hyperopia, astigmatism, and other ophthalmic conditions by inducing changes in the cornea of the eye, including the cornea's dioptric power.

BACKGROUND OF THE INVENTION

Of the four refractive interfaces of the eye, the anterior surface of the cornea provides most of the refractive power of the eye. Therefore, various surgical techniques have been developed which change the curvature of the cornea in order to treat ophthalmic conditions involving errors of refraction such as myopia and hyperopia. These techniques include keratotomy, keratomileusis by a freezing process, automated lamellar keratomileusis (ALK), photo-reactive keratomileusis (PRK), laser-assisted in situ keratomileusis (LASIK), laser intrastromal keratomileusis, laser epithelial keratomileusis (LASEK), conductive keratoplasty (CK), and scleral resection (see published US Patent Application 2003/0139737; U.S. Pat. No. 5,144,630; U.S. Pat. Nos. 5,520,679; 5,484,432; 5,489,299; 5,722,952; 5,465,737; 5,354,331; 5,529,076, 6,258,082; 6,263,879; each of which is incorporated herein by reference). All of these techniques work by using various techniques to change the curvature of the cornea, but they are limited by how much refractive error can be corrected and the type of patients who can be treated using these techniques (e.g., in some patients the cornea is too thin to safely utilize techniques which would further thin the cornea). Some of the techniques involve making incisions in the cornea with a diamond knife and/or ablating areas of the cornea thereby increasing the risk of infection or other complications. These techniques also largely depend on the dexterity of the surgeon performing the procedure, his or her surgical experience, and his experience performing laser ablations (e.g., with a Er:YAG (at 2.94 microns), Ho:YAG laser (at about 2 microns); Raman-shifted solid state laser (at 2.7-3.2 microns), or optical parametric oscillation (OPO) laser (at 2.7-3.2 microns).

Even more modern techniques are limited by their ability to cut corneal or sclera tissue with the desired precision causing a small, or even moderate, amount of refractive error to remain after the procedure and not allowing one to achieve the desired vision for near and for far in one single surgical procedure. The remaining refractive error may also be irregular making it more difficult to correct in the future. When one can not meet the visual demands that the patient requires, the ophthalmologist must resort to additional methods to correct the remaining refractive error. This is usually done by prescribing eye glasses, prescribing contact lenses, or performing a second surgical procedure (commonly known as a "retouch"). Therefore, limitations on the correction of refractive error using these techniques are significant, and the risk of having uncorrectable vision even with a secondary measure is considerable.

In addition, attempts to treat presbyopia using these techniques have also had very limited success. Presbyopia, also known as short arms disease, is a lack of lens accommodation, which prevents the eye from changing its focus. This phenomenon eventually occurs in all individuals over the age of forty. Accommodation allows an individual to see nearby objects by causing both eyes to converge on a near focal point, the pupil to shrink (myosis), and the lens to increase its dioptric power, thereby increasing its curvature in order to focus the image of nearby objects on the retina. Typically, young children have a total accommodation of 14 diopters. As a person ages, the lens of the eye becomes larger, thicker, and less elastic. These changes in the lens are largely due to the progressive denaturation of proteins in the lens. As the ability of the lens to change shape decreases, the power of accommodation decreases from approximately 14 diopters in young children to less than 2 diopters at the age 45 to 50 and to about zero at age 70. Once a person reaches the state of presbyopia, the eye remains focused permanently at an almost constant distance, which is largely determined by the physical characteristics of the individual's eye. The eye can no longer accommodate to see both near and far requiring an older person to wear bifocal glasses with the upper segment for seeing far and the lower segment for seeing near.

This general view of accommodation and presbyopia also does not take into account other aspects of the visual system. For example, this view does not take into account the higher cognitive functions necessary to orchestrate the eyes, the muscular system, and the brain including the visual cortex in the process of accommodation. The monovision techniques described above (e.g., the myopization of one eye, LASIK monovision), the different techniques that cause positive areas in the central zone of the cornea by making changes in the peripheral curvature, and the sclera resection or implants to change the scleral rigidity, cilliary muscle, and zonule, and increase the accommodation power of the lens among other more invasive techniques have had very limited success in treating presbyopia. These disappointing results may stem from a variety of sources including the lack of full understanding of the physiological behavior of the eye and its connections with the brain, the nervous system, and the muscular system, the imprecise measurement of the refractive power of the cornea and lens, and the lack of precision in surgical techniques performed by human surgeons.

Ophthalmologists have begun to use sophisticated equipment to measure various parameters of the eye in order to treat presbyopia. However, even the most sophisticated measurements are just approximations due to the fact that the cornea and other parts of the eye are similar to a fingerprint in that there are numerous variations which cannot be adequately described by a finite set of parameters. Also, it is impossible to precisely know how the cornea, lens, retina, and other parts of the visual system will react after surgery under different conditions (e.g., near and far visual stimuli). Furthermore, it is impossible to know how the cornea will heal after refractive surgery (e.g., the final radius of curvature).

The limitations on the existing treatments of presbyopia stem from the fact that these techniques consider only one anatomical region of the eye (i.e., the cornea or the lens). Any correction of near vision in turn causes the far vision of the subject to diminish. In addition, these current techniques model the eye using, among others, Gullstrand's model of the eye which neglects the individuality and uniqueness of each subject's eyes. For example, the ocular globe is not a perfect sphere. Although there are many mathematical models of the eye and its components used in calculating corneal power and the power of the globe (e.g., ray tracing), Gullstrand's model is probably the most popular.

Therefore, a need remains for a successful, non-invasive treatment of presbyopia. Presumably, this treatment could also be used to treat other ophthalmic conditions involving refractive errors including myopia, hyperopia, and astigmatism.

SUMMARY OF THE INVENTION

The present invention provides a system for treating ophthalmic conditions such as presbyopia, myopia, hyperopia, astigmatism, and other conditions involving errors in refraction of the eye. The system alters the corneal physiology, including the dioptric power of the cornea, through a dynamic and interactive technique which alters the shape of the cornea, thereby altering its refractive power. The patient being treated guides the treatment with respect to his or her visual needs, and the physician or optometrist uses this feedback from the patient as well as information regarding the age of the patient, the patient's visual needs (e.g., work habits, daily life), the patient's visual acuity, measurements of the eye, etc. to design the proper treatment regimen. In this way, the individuality of each person being treated and his or her eyes is taken into account during the treatment procedure. The treatment involves wearing a set of prescribed contact lenses to reshape the cornea and administering a pharmaceutical composition (e.g., eye drops) formulated for the patient to allow for reshaping of the cornea.

One of the many advantages of this system is that changes in the cornea are made without utilizing any type of surgery. Another advantage over current treatments is that the inventive system is dynamic, gradual, and interactive; therefore, it can be adjusted or repeated as many times as necessary to meet the visual needs of the patient. Also, the changes induced in the cornea are reversible. For example, the technique may need to be repeated due to progression of the disease, changes in visual acuity, aging, changes in working habits, changes in reading habits, etc. Preferably, the visual needs of the patient are met with the first treatment.

First, to achieve fine adjustments in the curvature of the cornea, instruments are used to measure the refractive power of the cornea, the curvature of the cornea, the thickness of the cornea, and the shape of the ocular globe (i.e., the total power of the eye). After these initial measurements are made and the change in curvature of the cornea to be induced is determined, a set of contact lens is prescribed for use by the patient. The contact lenses are chosen based on their different base curves in the posterior and anterior curvature radius as well as its optical diameter and multiple peripheral zones to induce changes in the corneal physiology and anatomy. In certain embodiments, the contact lens exerts pressure on the central zone of the cornea, thereby flattening the cornea and taking out dioptric power. In other embodiments, the contact lens exerts pressure at the periphery of the cornea, thereby steepening the cornea and adding dioptric power. The contact lenses constantly, gradually, and uniformly change the shape of the cornea to achieve the desired shape and thereby the refractive power needed by the patient. The contact lenses used in the inventive system are preferably off-the-shelf rigid or soft contact lenses that already exist commercially. Preferably the contact lenses are not specifically designed for orthokeratology. The contact lenses may be specially made for the patient being treated, or the contact lenses may be specially made for orthokeratology. The wearing of the contact lenses will be determined by various factors including the desired change in the cornea, the visual memory of the patient, the patient's age, the patient's tolerance of the lenses, the duration of the treatment, the pharmaceutical composition prescribed, etc. In certain embodiments, the contact lenses are worn several hours per day (e.g., 2, 3, 4, 5, 6, 7, 8, 9, 10, 11, or 12 hours per day) or all day long for several weeks (2, 3, 4, 5, 6, 7, 8, 9, 10 weeks) until the desired changes have been made. In certain embodiments, the contact lenses are worn overnight. The contact lenses used in the treatment may be changed over the course of the treatment as determined by the ophthalmologist with consultation with the patient. The present invention may change the dioptric power of the cornea by up to 5 Diopters, preferably up to 4 Diopters.

As well as wearing the contact lenses, the patient must also use a pharmaceutical composition, preferably eye drops, suitable for delivery to the eye that allows the cornea to be more readily molded. The pharmaceutical composition may also stabilize, improve, increase the change of the corneal curvature, or reduce the incidence of undesired side effects. In certain embodiments, the composition enhances the mechanical stress on the eye exerted by the contact lens over the surface of the cornea. These eye drops typically contain enzymes such hyaluronase and/or collagenase, and/or other agents such as carbamide (urea). In certain embodiments, the pharmaceutical composition also contains a vehicle such as methylcellulose or polyvinyl alcohol. The formulation of the eye drops is adjusted depending on various factors such as the age of the patient, the degree of change being made in the cornea, the physiology of the patient's cornea, the disease being treated, the duration of the treatment, etc. The eye drops may also contain other ingredients such as lubricants, vitamins, antibiotics, anti-inflammatory agents, anti-allergics, immunosuppressants, vasoconstrictors, and anesthetics. The eye drops may be in a liquid, spray, or gel form. Typically, the eye drops are administered at least once per day. In certain embodiments, the eye drops are administered once, twice, three times, four times, or five times per day. In other embodiments, the eye drops are administered every five minutes, every fifteen minutes, every half hour, every hour, every two hours, or every three hours. The use of the eye drops is continued for as long as the patient wears the contact lenses. The present invention provides pharmaceutical compositions to be used as eye drops in the treatment method. The inventive pharmaceutical compositions may also useful in combination with refractive surgery, in treating patients with low or moderate refractive error, and in preventing presbyopia.

In certain embodiments, the pharmaceutical agents found in the eye drops are included in the contact lenses. For example, the contact lenses are impregnated or coated with the agents so that the wearing of the contact lenses provides continuous deliver of the agents. Any of the agents described herein such as hyaluronidase, collagenase, vehicle, anti-inflammatory, lubricants, antibiotics, etc. may be added to the contact lenses for time-release delivery of the agent(s). This manner of delivering the agents is particularly useful when the contact lenses are worn at night while the patient is sleeping.

The inventive treatment system is useful in treating ophthalmic conditions such as presbyopia, myopia, hyperopia, and astigmatism. The treatment system may also be used in treating other diseases involving refractive error. Preferably, the inventive system is the first line of treatment for these conditions. In other embodiments, the patient may have already undergone a more traditional treatment such as LASIK or PRK, and the inventive system may be used to further correct any residual refractive error remaining after the first procedure. This allows correction of any remaining error without an additional surgery. The residual refractive error is commonly due to the lack of an exact measurement of the refractive defect before the surgery but can be due to other causes as described above. Therefore, the best way to correct the residual error is using a dynamic and interactive technique such as the inventive method in order to gradually change the curvature of the cornea until the patient finds that his or her visual needs (i.e., the corneal power is sufficient for the patient's visual needs based on the patient's visual memory and cerebral accommodation) for near and far vision are met. In certain embodiments, the corneal power is not corrected perfectly because this may prevent the seeing near or far. Instead, the patient may rely on other compensatory measures to achieve perfect vision under various circumstances, such as low light, fatigue, seeing far away, seeing close up, reading, etc.

In one aspect, the present invention provides a kit containing items useful in treating ophthalmic conditions such as presbyopia using the inventive method. The kit may contain all or some of the following: reservoir for contact lens, solutions for cleaning and/or disinfecting contact lenses, at least one pair of contact lenses, back-up contact lenses, eye drops as described above, lubricants, eye charts, mirror, and instructions for the patient. Preferably, the items of the kit are packaged in an ergonomic case which preferably is portable.

In another aspect, the present invention provides software useful to the treating ophthalmologist, optometrist, nurse, or other health care professional. Certain information about the patient is entered into the program running on a computer. This information may include name, age, sex, profession, description of visual needs, visual acuity, keratometry, retinoscopy, etc. The operator of the software may then be asked a series of questions (e.g., rigid or soft contact lenses. From the data entered into the program, the software may determine the type of contact lenses to be used (e.g., soft or hard), the power in diopters, the posterior base curve, the posterior peripheral curvature, the anterior curve, the anterior peripheral curve, diameter of central zone, and the diameter of the peripheral zone. The software may also be used to determine the composition of the pharmaceutical composition to be prescribed to the patient and/or the dosing regimen.

DEFINITIONS

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). In certain embodiments, the animal is a human.

"Cerebral accommodation": Cerebral accommodation refers to any functions that control the movements of the muscles involved in the optical-cerebral-motor system. Cerebral accommodation is necessary to focus the image in order to see well both near and far objects. In certain instances, cerebral accommodation refers to the reflex arcs and the muscle and nervous stimuli that are needed to achieve the proper movements of the body (e.g., head, neck) and eyes in order to see well near and far.

"Corneal power": Corneal power refers to the mathematical value expressed in diopters of the corneal refractive power or in millimeters when referring to curvature radius. Corneal power refers to the mathematical value of refractive power that is needed to meet the demands of the visual system including visual memory and cerebral accommodation. To measure the corneal power, it is necessary to determine the radius of anterior curvature, the corneal thickness, and the radius of posterior corneal curvature. In most instances, the corneal power cannot be measured exactly because all the different anatomical areas contributing to corneal power cannot be measured. Corneal power may also change during the day (e.g., due to fatigue) and from day-to-day.

"Induction of change in corneal power" refers to the mathematical change in diopters or in millimeters of curvature radius, of the value of the radius of the anterior corneal curvature that is to be induced to achieve the necessary dioptric power to change the corneal refraction power and thereby to achieve the near and far vision required by the patient in each eye.

"Effective amount": In general, the "effective amount" of an active agent or a pharmaceutical composition refers to the amount necessary to elicit the desired biological response. As will be appreciated by those of ordinary skill in this art, the effective amount of an agent may vary depending on such factors as the desired biological endpoint, the agent being delivered, the disease being treated, the subject being treated, etc. The effective amount of hyaluronase in the pharmaceutical composition is the amount necessary to degrade enough hyaluronic acid molecule to allow for molding of the cornea. The effective amount of collagenase in the pharmaceutical composition is the amount necessary to degrade enough collagen to allow for molding of the cornea. The effective amount of carbamide in the pharmaceutical composition is the amount necessary to allow for molding of the cornea.

"Molding contact lens": Molding contact lenses are any contact lenses that are used with the inventive method and system. The lenses may be particularly designed for molding the cornea to a shape in some embodiments. However, in other embodiments, the molding contact lenses are not especially designed for the inventive system but are instead off the shelf contact lenses typically worn by a patient to correct visions. The molding contact lenses may be rigid or soft, permeable or non-permeable. The molding contact lens are typically made of a plastic, polymer, or glass. In some embodiments, the molding contact lenses include pharmaceutical agents helpful in molding the cornea to a particular shape.

"Optical-cerebral-motor system": The optical-cerebral-motor system refers to the anatomical structures of the body that by interconnections (e.g., nerves) interact to carry out the muscular adjustments of the body and of the ocular globe to achieve an adequate position and to be able to activate the reflexes, voluntary, and involuntary movements necessary for seeing objects near and far. The system may include the visual cortex, the motor cortex, muscles of the head and neck, muscles of the eye, optic nerves, cranial nerves, and eyes.

"Point of dispersion": Point of dispersion is the point at which divergent rays would intersect if traced backward. The point of dispersion can also refer to an image of an object or a visual stimulus that characterizes an optical system.

"Stromal sliding": Stromal sliding is the displacement of the corneal stroma after any refractive surgery performed on the cornea. Stromal sliding is due to the separation of the lamellae during the cutting or ablation of the cornmeal tissue. This allows the corneal wound to slide thereby flattening or steepening the corneal curvature during the healing process. Stromal sliding is also an important part of the inventive technique.

"Visual acuity": Visual acuity refers to the clarity or clearness of one's vision, a measure of how well a person sees. In certain embodiments, it refers to the Snellen acuity (e.g., 20/20).

"Visual memory": Visual memory refers to the accumulation of the images at the brain that are received through the optical-cerebral-motor system during one's lifetime. Visual memory starts to form when the first images arrive into the brain during childhood. The brain recognizes and perceives the wavelengths of light as images. The brain organizes all the images it accumulates and uses this information to react to visual stimuli and recognize objects (e.g., letters of the alphabet). The visual memory develops depending on how often certain types of stimuli are in front of the eyes. Developing visual memory may depend on sharpness of the images arriving at the retina or brain, physical and mental development, environmental influences, heredity, etc. The visual memory forms from images transmitted to the brain with or without correction (e.g., eyeglasses or contact lenses). Normally, visual memory will tolerate small discrepancies such as, for example, due to illness, stress, fatigue, etc. Visual memory allows the patient to compensate and carry on normal activities such as driving, reading, writing, drawing, playing sports, etc. Visual memory is important in the development of visual acuity and is used to orchestrate all the body's compensatory mechanisms, such as cerebral accommodation. For example, when the eye cannot transmit good quality images to the brain for a near stimulus, the visual memory reacts and starts to demand visual quality it has come to expect. The visual memory may turn on certain compensatory mechanisms such as cerebral accommodation. When the cerebral accommodation cannot compensate adequately, the patient may need to resort to other compensatory mechanisms such as squinting, turning up light levels, moving eyes further away or closer, using glasses, etc. For example, in reading a book, if the patient is fatigued, he or she may need to hold the book closer or turn up the light level in order to read. The corneal power is preferably adjusted so that the visual images transmitted to the brain are accepted by visual memory. The patient's own satisfaction and acceptance of the new images is preferably the way the corneal power has been corrected by the inventive system to the extent needed by visual memory.

DETAILED DESCRIPTION OF CERTAIN PREFERRED EMBODIMENTS OF THE INVENTION

Figure 1:
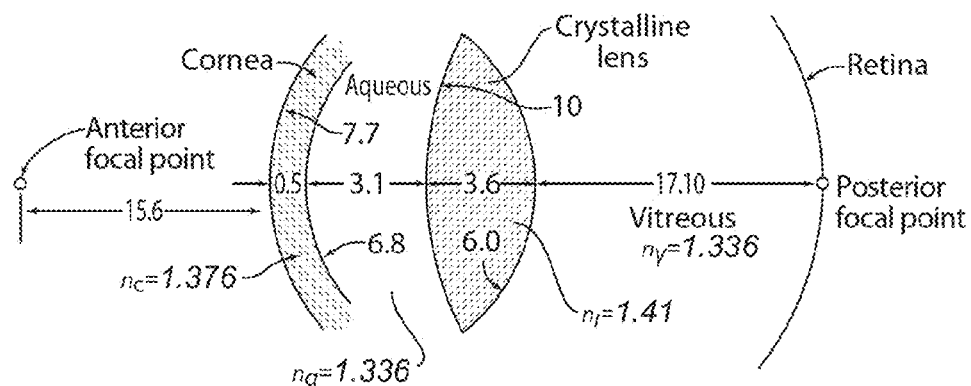
FIG. 1 is an illustration of Gullstrand's model of the eye. This model is used to calculate the refractive power of the cornea as well as other parts of the eye. Such a schematic is useful in determining the adjustments to the cornea needed in correcting the patient's vision.

The present treatment system is based on inducing a change in the curvature of the cornea (e.g., the anterior radius of the cornea). The change allows the patient to see better near and far without the need for eyeglasses, contact lenses, or other visual aids. The system works by inducing a compound myopic astigmatism with a vertical axis (horizontal or oblique) according to the visual needs of the patient being treated. The system is interactive and depends on input from the patient on how the treatment is to proceed. This is one of the differences between the inventive system and those already known in the art that essentially rely on detailed measurements of aspects of the eye by an ophthalmologist.

The methods used to induce changes in the anterior radius of the cornea include wearing molding contact lenses after refractive surgical techniques such as LASIK, LASEK, PRK, CK, or other surgical procedures that alter the anterior layers of the cornea or the sclera or any change or alteration in the refractive power of the eye; wearing molding contact lenses and using a pharmaceutical composition suitable for administration to the eye when the refractive error is low to moderate, when the patient has been operated on and the healing process is already complete, or when the patient has had no surgeries but is suffering from presbyopia, myopia, hyperopia, astigmatism, or other ophthalmic condition. The method is a dynamic and interactive technique in that the normal physiology of the cornea is altered at the same time the visual memory and cerebral accommodation of the patient is altered to achieve the refractive power of the cornea necessary to achieve the desired near and far vision of the patient. The inventive method alters the cornea in a gradual, continuous, programmed, and controlled way without producing irreversible changes or undesired complications. In certain embodiments, the method alters the cornea in a uniform manner. In other embodiments, the change induced is not uniform (e.g., in treating astigmatism). The patient plays an important role in guiding the treatment to achieve the desired vision much like a photographer focusing the lens of a camera.

Any patient with a refractive error can be treated using the inventive system. Ophthalmic conditions treatable using the inventive system include presbyopia, hyperopia, myopia, astigmatism, and any other ophthalmic condition that can be treated by changing the shape of the cornea. In certain embodiments, the patient suffers or is at risk of suffering from presbyopia. Certain patients have had good visions for near and far vision, have never needed eyeglasses or contact lenses, but could develop presbyopia with increasing age resulting in diminished near vision. In other embodiments, the patient is born with a refractive defect (e.g., a genetic refractive defect), and the patient desires to correct the defect in any one of the different distances—near, intermediate, or far. In yet other embodiments, the patient has undergone surgery to correct a refractive error but a residual defect in refraction remains in near, far, and/or intermediate vision. In certain embodiments, the patient under 18 years of age is treated for a refractive defect so that when he or she reaches the age of 40 and the symptoms of presbyopia begin, the changes in the refractive power of the cornea can be minimized and therefore better accepted by the patient (e.g., visual memory, cerebral accommodation) without inconvenience or discomfort.

Cerebral accommodation is a natural process. Cerebral accommodation is based on a function of the brain, specifically the function allowing the images to form through the visual organ and to execute the muscular actions used to initiate and complete the reflexes that interconnect the optical and motor systems. Once images are captured by the eye, they are sent to the brain (visual cortex) and stored in visual memory. The visual stimuli during the normal development of each individual varies and this is why cerebral accommodation plays such a key role in carrying out functions that the individual apparently carries out unconsciously. The inventive system therefore takes into account cerebral accommodation in the treatment of the patient. The transmission of the unfocused, blurry image becomes very difficult to associate and to interpret with the other images in visual memory at the onset of presbyopia when the eye and the nervous system are not in sync. As a result the patient requires the use of eyeglasses. The inventive technique molds the cornea to achieve the near and far vision that the patient requires to meet the demands of the visual system including the visual cortex and visual memory.

Figure 2:
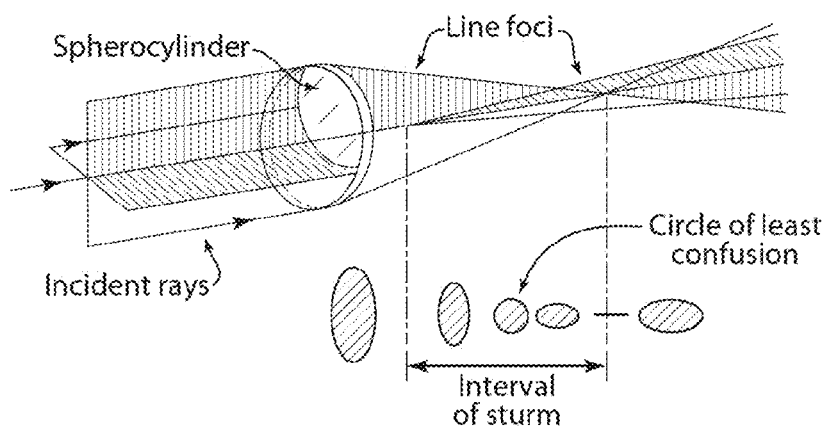
FIG. 2 is an illustration of the Sturm's conoid used to show the formation of an image by a sphero-cylindrical lens.

The invention is better understood by considering the Gullstrand's model of the eye (FIG. 1) and the conoid of Sturm (FIG. 2). As will be appreciated by others of skill in this art, other models of the eye may also be used mathematically model the visual system. The model of Gullstrand shows the elements for the calculation of the refractive power of the cornea in accordance with the present invention using old and traditional mathematical concepts. This calculation of the refractive power of the cornea is based on the radius of curvature of the anterior surface of the cornea, the corneal thickness, and the radius of curvature of the posterior surface of the cornea.

The initial measure of the radius of curvature of the anterior surface of the cornea is obtained by keratometer measurements. The measurement is done directly in diopters if the refractive index as determined by the keratometer is the same as used in the calculation by the treating physician. Preferably, the measurement is done in the same units as used by the treating physician. In addition, it is preferably that all instruments used in the invention are calibrated together. In certain embodiments, the measurement of the initial radius ($R_i$) is made in millimeters and then converted to diopters using the following formula:

$$D=[(n-n')\times 1.000]/R$$

where D=diopters, n=refractive index of air, n'=refractive index of the cornea, R=radius of curvature of the anterior surface of the cornea, $R_i$=initial radius, and $D_i$=initial diopter.

Estimate of the Refraction Defect

The amount of the refractive defect in the eye is measured in the corneal vertex with the following formula:

$$D_v=D_c/[1-(xD_c/1.000)]$$

where $D_v$=diopters to vertex, and $D_c$=diopters of correction.

Then the final diopters are calculated by the following formula:

$$D_f=D_i+D_v=332/R_i+D_v$$

where $D_f$=final diopter, $D_i$=initial diopter, $R_i$=initial diopter, and $D_v$=diopters to vertex.

Final Radius

The final radius of curvature of the anterior surface of the molded cornea is calculated in millimeters, instead of diopters, to facilitate use with different measuring equipment. The final radius is calculated using the following formula:

$$R_f=332/[(332/R_i)+D_v]$$

where $R_f$=final radius, $R_i$=initial radius, and $D_v$=diopters to vertex.

Corneal Thickness

The corneal thickness is calculated based on the difference between the radius of curvature of the anterior surface and the radius of curvature of the interface (the ablation obtained in the anterior stroma).

Radius of Posterior Surface

The radius of curvature of the posterior surface is equal to the final radius minus the post-surgical stromal thickness ($R_{sp}=R_f-E_d$).

The calibration of the optical equipment is based on the Gullstrand's model of the eye. When there is a large change in any one of the parts of the eye being measured (e.g., the radius of curvature, the thickness of the cornea, the index of refraction), it is no longer possible to precisely measure the refractive power of the cornea in the majority of automated optical equipment (e.g., the auto-kerato-refractometer). Consequently, to be able to carry out the exact mathematical calculations it is necessary to utilize equipment that actually measures the radius of curvature of the anterior surface, the corneal thickness, and the radius of curvature of the posterior surface (e.g., ORBSCAN II, commercially available from Bausch & Lomb Surgical). This type of equipment, in general, measures the refractive power of the cornea in very large increments (e.g., 0.25 D), which causes errors for the correct measurement of the vision of the patient and consequently to obtain the mathematical formula for the calculation of the refractive power of the cornea that is required to reach the desired near and far vision for the patient.

In the present invention, the induced refractive power of the cornea is considered similar to a sphere (myopia) and a myopic cylinder (astigmatism) of 0.100 of diopters to 0.999 of diopters, that is the recommendable range to be able to correct the near vision without diminishing significantly the far vision. Myopic astigmatism is from sphere −0.100 to −0.999 D. Hyperopic astigmatism is from sphere +0.100 to +0.999 D. The cylinder in astigmatism is −0.100 to −0.999. The axis of astigmatism can be 0° to 360°. As will be appreciated by one of skill in this art, the visual quality and visual capacity will also be related to pupil diameter.

The entire visual system including the lens, zonule, ciliary muscle, ciliary body, sclera, brain, visual cortex, and visual memory are considered in the dynamic and interactive system of the present invention. Each of part of the eye plays an important role in vision, and modifications of each of these parts either iatrogenically or by aging causes changes in the vision of the patient.

Once the measurements and calculations above have been measured, the patient is consulted to determine his or her visual needs both for near and far vision. This is based on the fact that the patient is the one who really measures, feels, and relies on his or her refractive power of the cornea. The person administering the treatment can then use this information in approaching the mathematical formulae described above. This combined approach guides the treatment of the patient in determining the steepness or flatness to be induced in the patient's cornea.

To carry out the reshaping of the patient's cornea, the inventive system combines the use of molding contact lenses and a pharmaceutical agent suitable for administration to the eye (e.g., eye drops). In certain embodiments, computer software is used to determine the contact lenses most suitable for the patient and/or to determine the formulation of the pharmaceutical agent.

The software of the invention prompts the health care professional (e.g., ophthalmologist, optometrist, nurse, etc.) to enter certain information about the patient. This information may include name; age; sex; profession; near working distance; tolerance to contact lenses (if the patient has used them before), optometric data; visual acuity (e.g., near, far, with both eyes, each eye separately, corrected, or uncorrected); keratometry; topography; paquimetry (thickness of the cornea); wave front; ray tracing measurements; retinoscopy with normal pupil; refraction with normal pupil; best corrected visual acuity (e.g., far or near, both eyes or each eye separately); retincoscopy with mydriasis; refraction with mydriasis; best near vision for vision at 45 to 55 cm, for Jaeger 3, for Jaeger 4, or for Jaeger 5; etc. Any of the input data described above may be included or excluded from the program's determination of the contact lenses or pharmaceutical composition to be used by the patient. The software may also allow the conversion of keratometry from diopters to millimeters. The user may be prompted to choose a flatter, steeper, or average keratometry. The user may be asked to choose between soft or hard contact lenses for the patient. The user may be asked to enter posterior base curve, peripheral posterior curve, anterior curve, and/or anterior peripheral curve. The user may also be asked to choose the power. In certain embodiments, the software uses the entered data to determine the contact lenses to be used by the patient. The software may determined soft versus hard contact lenses, power in diopters, posterior base curve, posterior peripheral curvature, anterior curve, anterior peripheral curve, diameter central zone, and/or diameter peripheral zone. In certain embodiments, the software will determine the composition of the pharmaceutical composition and/or the dosing regimen for the pharmaceutical composition.

In a certain embodiment, the software begins by prompting the user for the following patient data: name, age, right eye keratometry, right eye paquimetry (thickness of cornea), right eye ocular defect, left eye keratometry, left eye paquimetry (thickness of cornea), left eye ocular defect, and whether the patient has worn contact lenses before. If the patient has worn contact lenses before, the user is prompted to enter information regarding what type of contact lenses they were and whether they were comfortable. For the patient who has never worn contact lenses, the user is asked to select the patient's sensitivity level (e.g., high, low, null). After the information is entered, the software confirms that all data has been entered and that the information falls within certain ranges. For example, the patient's age must be between 1 and 100 years. The right and left eye keratometry must be between 34.09 and 55.32 D. The paquimetry of both eyes must be a value between 450 and 650 microns. The user is asked to confirm all the entered data to reduce the chance of error. After all the data has been entered, the software then calculates the results using the formula described herein. The software determines the type or contact lens recommended for the patient and the base curve expressed in millimeters. When the defect is larger than 2 D, the message "Define lens power depending on patient". When the keratometry value of any eye is less than 40 or larger than 48 D, the following message will appear "Define peripheral base curve."

The inventive method for treating a patient suffering from a disorder involving refractive error such as presbyopia includes assessing the patient (e.g., age, working needs of the patient, eye disease, etc.), prescribing the use of molding contact lenses to induce the needed changes in the radius of curvature of the anterior surface of the cornea, and prescribing the use of a pharmaceutical composition to be used in conjunction with the contact lenses.

The present system can be used to induce a change in the refractive power of the cornea by inducing a change in the radius of curvature of the anterior surface of cornea with a myopic range (sphere) of −0.25 D to −0.75 D or with a myopic astigmatism (cylinder) of −0.25 D to −0.75 D. By inducing a change in the refractive power of the cornea with myopia (sphere) greater than 1.00 D or more than 1.00 D in astigmatism (cylinder), the near vision is improved but the far vision diminishes. In certain preferred embodiments, the range for correcting the near vision without diminishing the far vision substantially is 0.100 D up to 0.999 D. To determine the best axis of astigmatism that the patient requires for near vision, each eye is evaluated separately.

In other embodiments, the change is induced in the refractive power of the cornea with a vertical axis of myopic astigmatism (e.g., in the case of vertical astigmatism with less than 45° with respect to the vertical (90°)).

The inventive method is particularly useful because it allows the treatment each eye of every patient to be completely personal. The treating physician is not limited to the measuring equipment or the available eyeglasses or contact lenses in treating the patient's visual error. Therefore, the precision of the correction is not limited to 0.100 D but instead can be performed with a greater degree of precision (e.g., 0.01 D, 0.005 D, 0.001 D, 0.0005 D, or 0.0001 D). The patient guides the treatment according to his or her visual needs. The treating physician can stop or alter the treatment as needed.

As described above, the currently existing instruments that are used to measure the extent of myopia or astigmatism do not measure the value of the radius of curvature of the anterior surface of the cornea, the corneal thickness, or the radius of curvature of the posterior surface of the cornea with the required precision.

The molding contact lenses which are prescribed and worn by the patient exert a mechanical force on the anterior surface of the cornea thereby inducing a change in the refractive power of the cornea. In certain embodiments, the molding contact lenses are hard or rigid molding contact lenses. In other embodiments, the molding contact lenses are soft contact lenses.

Once the molding contact lenses is placed on the eye of the patient, a pharmaceutical composition (e.g., eye drops) that allows for molding of the cornea is administered to the eye and/or reduce the connections between the corneal lamellae. The contact lenses and the pharmaceutical composition together produce the change in the refractive power of the cornea. The more frequently the pharmaceutical composition is administered the more quickly the corneal lamellas will adopt the desired change in shape. In certain embodiments, the composition is administered at least every 8 hours. In other embodiments, the composition is administered every 6 hours. In certain other embodiments, the composition is administered approximately every 3 hours. In yet other embodiments, the composition is administered approximately every two hours. In other embodiments, the composition is administered every one hour. The composition may be hypertonic (5% to 40%, preferably approximately 10, 20, 30, or 40%) or hypotonic (0% to 5%, preferably approximately 1, 2, 3, or 4%) depending on the needs of the patient (e.g., working needs, rest hours, sleeping, etc.) A hypertonic pharmaceutical composition (e.g., 40%) is typically used when a faster result is desired.

Figure 4:
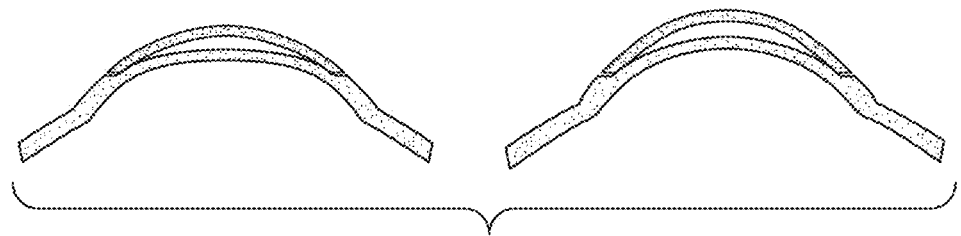
FIG. 4 is a schematic view showing stromal sliding.
Figure 5:
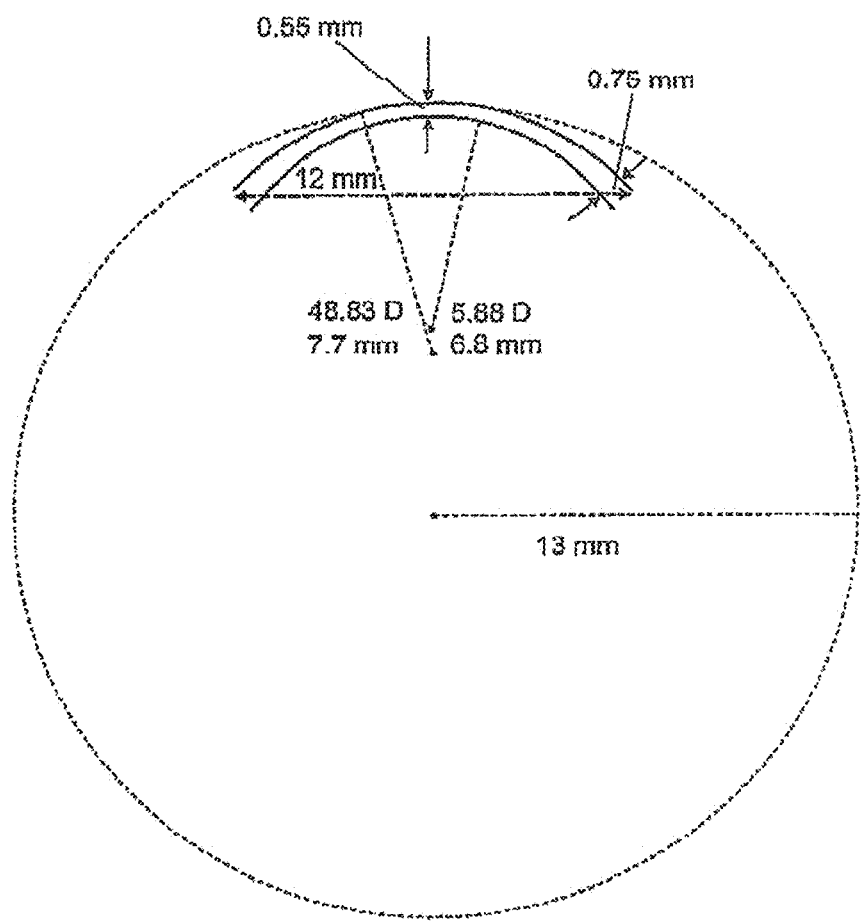
FIG. 5 depicts a mathematical model of the eye. The drawing shows the theoretical measurements needed to calculate corneal power and the ocular globe dioptric power. Note that this traditional model of the eye uses a sphere to present the ocular globe and mathematical constants in the cornea.
Figure 6:
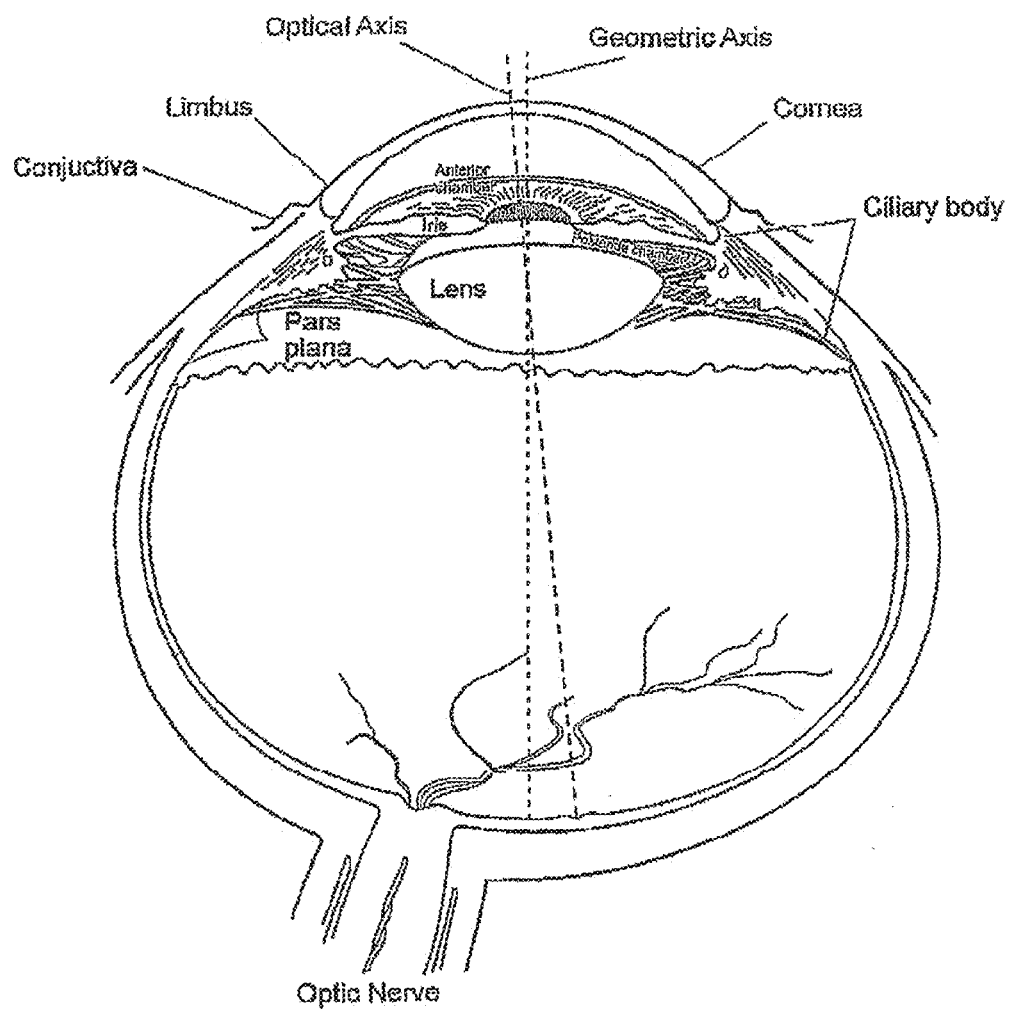
FIG. 6 shows a normal eye. The normal eye is not in fact a sphere. It has various anatomical irregularities and differences, and the optical axis is off center from the geometric axis.
Figure 7:
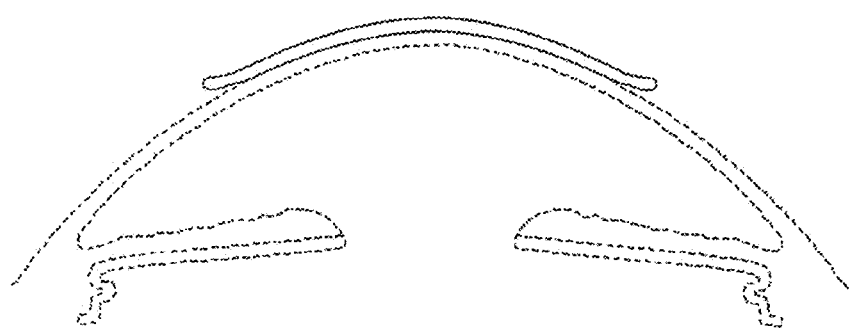
FIG. 7 shows a small centered contact lens on top of the cornea. Using this contact lens, pressure is applied to the central zone of the cornea. The peripheral zone is not touched by the contact lens. Pressure on the central zone of the cornea will flatten the central cornea and lessen the dioptric power of the cornea.
Figure 8:
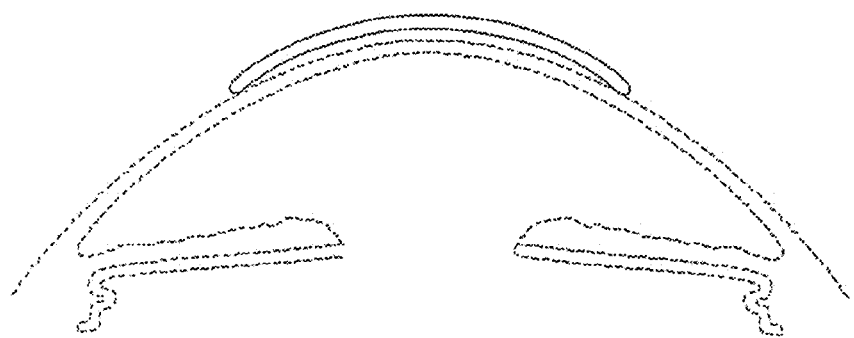
FIG. 8 shows a small centered contact lens on top of the cornea. The contact lens is exerting pressure on the peripheral zone of the cornea. The central zone of the cornea is not touched by the contact lens. Pressure on the periphery will steepen the central cornea, thereby adding dioptric power to the cornea.
Figure 9:
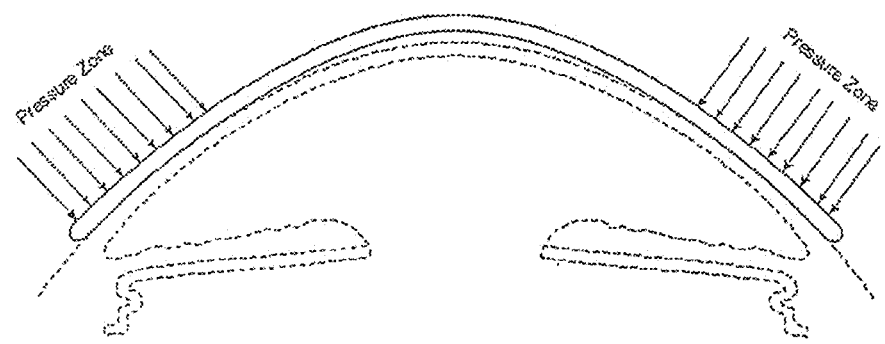
FIG. 9 shows a larger centered contact lens on top of the cornea. The contact lens is applying pressure to the peripheral zone of the cornea. This peripheral pressure will cause the central portion of the cornea to steepen, thereby adding dioptric power to the cornea.
Figure 10:
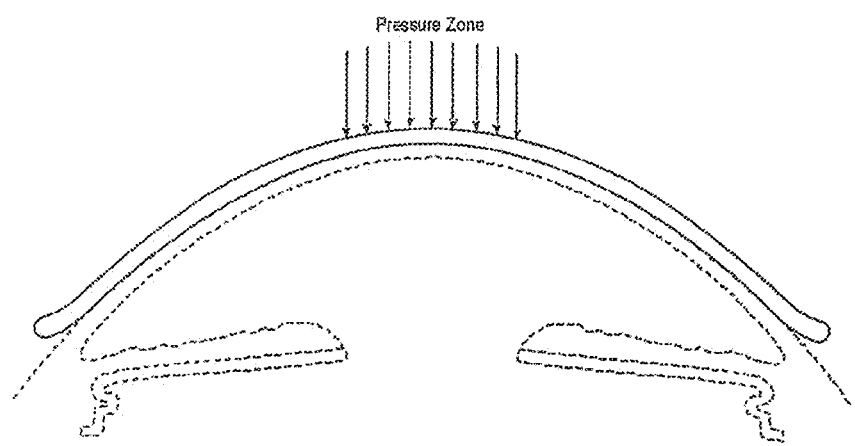
FIG. 10 shows a larger centered contact lens on top of the cornea. In this figure, the contact lens is exerting pressure on the central zone of the cornea. This pressure on the central zone will flatten the cornea and take out dioptric power from the cornea.

Without wishing to be bound by any particular theory, the inventive system is thought to work by the following mechanism. After any refractive surgical technique that cause spaces among the stromal lamellas either by cuts, resections, or ablations, a stromal sliding will cause the stroma to slide toward the periphery to correct more myopic defect or slide toward the center of the cornea to correct hyperopia or presbyopia (see FIG. 4). When molding contact lenses are used in conjunction with a pharmaceutical composition that enhances the mechanical force of the contact lenses, the corneal stroma is altered along with its anatomical and histological structures. The contact lenses and pharmaceutical composition induce changes in the mechanical force of the molecular structure (e.g., lamellas) and induce changes in the cells and proteins such as collagen and hyaluronic acid found in the corneal stroma. The surface of the cornea becomes more uniform by molding the corneal stroma. All healthy corneas have some irregularities in the surface as has been shown by isometric tomography and ultrasound. In the inventive system, the quality and clearness of all images (i.e., visual acuity) is improved by making more uniform the surface of the cornea.

For the calculation of the molding contact lenses the flattest keratometry is taken. One of skill in this art could also use the steeper keratometry or an average of both and based on this corneal curvature make the necessary calculations to flatten or steepen the radius of curvature of the anterior surface of the cornea and thus correct the refractive defect of the eye. The base curve of the molding contact lens is calculated based on the change in the refractive power for each eye separately. The base curve of the molding contact lens is calculated starting with one to four flatter or steeper diopters, more preferably one to three flatter or steeper diopters, even more preferably one to two flatter or steeper diopters, depending on the refractive error that is required. The peripheral base curve depends on the adaptation of the molding contact lens and is calculated to be 0.5 mm of radius greater than the central zone but can vary depending on the design. The diameter of the molding contact lens used in the inventive system is approximately 8.0 mm to 18.0 mm. These diameters are available commerically. In certain embodiments, the molding contact lens is a hard contact lens with a diameter ranging from 8.0 mm to 12.0 mm. In other embodiments, the molding contact lens is a soft contact lens with a diameter ranging from 13.0 mm to 15.0 mm. Soft contact lenses may cover the entire cornea and go from sclera to sclera. In certain embodiments, the molding contact lens is a combination of hard and soft materials. It may be hard in the middle out to approximately 12.0 mm, 13.0 mm, 14.0 mm, or 15.0 mm, and then soft in the periphery out to 16.0 mm, 17.0 mm, and 18.0 mm. A larger contact lens, preferably a soft contact lens, may be used at night as a molding contact lens. The power of the molding contact lenses is determined to the nearest possible refractive power that the patient requires to see comfortably. During the adaptation process with the molding contact lenses, if the vision is not adequate for the needs of the patient, the patient is prescribed eyeglasses while the patient is undergoing treatment.

As the cornea is being adapted or has been adapted, various optometric measurements are optionally repeated to confirm that the treatment is progressing as planned and is adequate. Such measurements may include visual acuity for near and far vision, the distance to see small print (J-3 to J-4) (e.g., print in a newspaper or magazine) satisfactorily, orthotypes, keratometry measurements, objective and subjective retinoscopy, diagram of the adaptation of the molding contact lens, movement of the molding contact lens, and comfort of the molding contact lens. After the measurements are taken, changes are made to the treatment program based on these measurements. Changes in the molding contact lenses and/or in the pharmaceutical compositions can be made to induce the desired refractive power in the cornea over the following weeks. In certain preferred embodiments, weekly periodic revisions are performed during the first 8 weeks after beginning treatment. In certain embodiments, if the patient has not undergone refractive surgery, then the pharmaceutical composition for administration to the eye should be prescribed.

The molding contact lenses used in the inventive system may be hard or soft. If a soft molding contact lens, a more positive or negative curvature is induce in the cornea, and the discomfort in the patient's eyes will diminish as he or she adapts to the contact lenses. If a hard molding contact lens is used, more mechanical pressure will be exerted on the cornea. In certain preferred embodiments, the contact lenses are gas permeable.

The pharmaceutical composition used in the inventive system includes agents that help to induce changes in the corneal lamellas, collagen fibers, hyaluronic acid, and the percentage of corneal hydration. Other aspects of the anatomy, histology, and physiology of the cornea may also be affected by the agents in the pharmaceutical composition. In certain embodiments, the composition may be hypertonic or hypotonic to induce changes in the percentage of corneal hydration. In other embodiments, the composition is used to change the sustentation forces of the molecular structure of the cornea (e.g., lamellas) and in this way mold the stroma to the desired curvature. In certain embodiments, the agents used in the pharmaceutical composition have been approved for use in humans by a regulatory agency such as the U.S. Food and Drug Administration (FDA) or an analogous foreign regulatory body. Preferably, the agents are approved for use in the eye.

In certain embodiments, the composition contains the enzyme hyaluronidase which is known to break down hyaluronic acid, which functions like a cement among the corneal lamellas. Hyaluronidase is an enzyme that degraded mucopolysaccharides by catalyzing the hydrolysis of the one to four linkages in hyaluronic acid, chondroitin, and chondroitin 4 sulfates A & C. Mucopolysaccharide is one of the intracellular ground substances (cement or glue) of the stroma, the connective-type tissue of the middle layer of the cornea. The shape of the cornea is largely dependent on the arrangement of collagen fibrils in the stromal layers of the cornea and on the arrangement of the mucopolysaccharides layers between these fibrils. Hyaluronidase breaks down the mucopolysaccharide chains when released into the cornea. The stroma of the cornea is thereby softened making it more amenable to reshaping by a molding contact lens.

Hyaluronidase may be obtained from a variety of natural sources from which the enzyme can be purified to at least 90% purity, at least 95% purity, at least 96% purity, at least 97% purity, at least 98% purity, or at least 99% purity. Natural sources include bovine (bull) testes, ovine (sheep) testes, and bacteria (*Streptomyces*). In certain embodiments, hyaluronidase is commercially available. For example, one form of hyalouronidase is available under the trade name WYDASE® (Wyeth Laboratories, Inc., Philadelphia, Pa.). The WYDASE® hyaluronidase is a preparation of highly purified bovine testicular hyaluronidase. The hyaluronidase enzyme may be supplied as a lyophilized powder. The powder can be reconstituted using phosphate buffer-saline solution. Typical proportions include approximately 150 USP units of hyaluronidase per 1 milliliter. In certain embodiments, the hyaluronidase is prepared using recombinant DNA technology. The hyaluronidase may be a modified version, e.g., a cleaved form, chemically modified, or genetically modified.

In certain embodiments, the concentration (weight percent) of hyaluronidase in the pharmaceutical composition ranges from 0.01% to 10%, or 0.1% to 7%, or 0.1% to 5%, or 1% to 5%. Increasing the concentration of hyaluronidase increases the ability of the contact lens to mold the cornea. In addition, the use of a vehicle such as a polymer (e.g., methylcellulose, polyvinyl alcohol, cellulose, etc.) in the composition allows the hyaluronidase to work on the cornea longer than without a vehicle.

It has been discovered that an effective amount of hyaluronidase for softening a cornea in a mammal is between approximately 50 units of enzyme per milligram of substrate (i.e., the mucopolysaccharide of the cornea) to approximately 5,000 units per milligram of substrate. Preferably, the effective amount is between 100 and 1,500 units per milligram of substrate. Higher doses may be administered to reduce the number of administrations necessary.

Other enzymes which may be included in the composition to soften the cornea include chondroitinase ABC, chondroitinase AC, keratanse, and stromelysin, which have been shown to work on various proteoglycan components of the cornea.

In certain embodiments, the composition contains the enzyme collagenase which is known to break down collagen, which functions as an extracellular matrix protein. In certain embodiments, the collagenase is prepared using recombinant DNA technology. In other embodiments, the collagenase is purified from a natural source. The collagenase may be a modified version, e.g., a cleaved form, chemically modified, or genetically modified. Other enzymes which break down the collagen components of the cornea include matrix metalloproteinase 1 (interstitial collagenase) and matrix metalloproteinase 2 (gelatinase). These enzymes may be used individually or in combination with other enzymes such as those that break down the proteoglycan component of the cornea. See U.S. Pat. Nos. 5,626,865 and 6,132,735, issued May 6, 1997 and Oct. 17, 2000, respectively, each of which is incorporated herein by reference. In certain embodiments, the pharmaceutical composition contains a combination of hyaluronidase and collagenase.

In certain embodiments, the concentration (weight percent) of collagenase in the pharmaceutical composition ranges from 0.01% to 10%, or 0.1% to 7%, or 0.1% to 6%, or 1% to 5%. Increasing the concentration of collagenase increases the ability of the contact lens to mold the cornea. In addition, the use of a vehicle such as a polymer (e.g., methylcellulose, polyvinyl alcohol, cellulose, etc.) in the composition allows the collagensase to work on the cornea longer than without a vehicle present.

In another embodiment, enzymes endogenous to the eye of the patient are used to soften the cornea. These endogenous enzymes are activated to begin the softening process. Metalloproteinzases are activated by the administration of interleukin-1α, tumor necrosis factor, monosodium urate monohydrate, 4-amino phenylmercuric acetate, human serum amyloid A, human $B_2$ microglobin, and copper chloride. See U.S. Pat. Nos. 5,626,865 and 6,132,735, issued May 6, 1997 and Oct. 17, 2000, respectively, each of which is incorporated herein by reference.

In certain embodiments, the composition contains the carbamide (urea). In certain embodiments, the carbamide is obtained from commercial sources. In other embodiments, the carbamide is purified from a natural source. The carbamide may be a derivative of carbamide or a salt of carbamide.

The pharmaceutical composition may also contain enzymes that degrade other sugars or proteins found in the cornea. In certain embodiments, the enzymes act to level the unions of the lamellas in the cornea. In other embodiments, the pharmaceutical composition alters the stromal hydration of the cornea or the corneal thickness. In other embodiments, an agent known to change the sustentation forces of the molecular structure of the cornea (e.g., corneal lamellas) is included in the pharmaceutical composition.

The pharmaceutical composition may contain other agents useful in the inventive procedure. In certain embodiments, the pharmaceutical composition contains an anesthetics used to reduce the irritation of the molding contact lens on the cornea. Examples of anesthetics include benzocaine, bupivacaine, cocaine, etidocaine, lidocaine, mepivacaine, pramoxine, prilocaine, chloroprocaine, procaine, proparacaine, ropicaine, and tetracaine. In other embodiments, the pharmaceutical composition includes a anti-inflammatory agent such as a steroid or a non-steroidal anti-inflammatory agent. Example of anti-inflammatory agents include aspirin, acetaminophen, indomethacin, sulfasalazine, olsalazine, sodium salicylate, choline magnesium trisalicylate, salsalate, diflunisal, salicylsalicylic acid, sulindac, etodolac, tolmetin, diclofenac, ketorolac, ibuprofen, naproxen, flurbiprofen, ketoprofen, fenoprofen, suprofen, oxaprozin, mefenamic acid, meclofenamic acid, oxicams, piroxicam, tenoxicam, pyrazolidinediones, phenylbutazone, oxyphenthatrazone, pheniramine, antazoline, nabumetone, COX-2 inhibitors (Celebrex), apazone, nimesulide, and zileuton. Glucocorticoids such as hydrocortisone, prednisolone, fluorometholone, and dexamethasone may also be used as anti-inflammatory agents. In still other embodiments, the pharmaceutical composition includes a lubricant. These agents are included to improve the comfort of the patient during the treatment. One of skill in this art based on the individual patient determines the composition of the eye drops being prescribed for the patient.

In certain other embodiments, the pharmaceutical composition includes anti-microbial agents such as anti-bacterial, anti-viral, and/or anti-fungal agents. Exemplary anti-microbial agents include bacitracin zinc, chloramphenicol, chlorotetracycline, ciprofloxacin, erythromycin, gentamicin, norfloxacin, sulfacetamide, sulfisoxazole, polymyxin B, tetracycline, tobramycin, idoxuridine, trifluridine, vidarabine, acyclovir, foscarnet, ganciclovir, natamycin, amphotericin B, clotrimazole, econazole, fluconazole, ketoconazole, miconazole, flucytosine, clindamycin, pyrimethamine, folinic acid, sulfadiazine, and trimethoprim-sulfamethoxazole.

The pharmaceutical composition may also include vasoconstrictors. Vasoconstrictors may include dipivefrin (propine), epinephrine, phenylephrine, apraclonidine, cocaine, hydroxyamphetamine, naphazoline, tetrahydrozoline, dapiprazole, betaxolol, carteolol, levobunolol, metipranolol, and timolol.

The pharmaceutical composition may also include vitamins or other nutrients such as vitamin A, vitamin $B_1$, vitamin $B_6$, vitamin $B_{12}$, vitamin C (ascorbic acid), vitamin E, vitamin K, and zinc.

The pharmaceutical composition may be provided in any form suitable for administration to the eye. For example, the pharmaceutical composition may be in the form of eyedrops, a semisolid gel, or a spray. In certain embodiments, the molding contact lenses are impregnated with the agents necessary to mold the stroma. In this manner, the agents can be delivered to the cornea continuously and in a time-release manner as the patient is wearing the contact lenses.

An exemplary pharmaceutical composition of the invention may include 5-10% anesthetic, 10-20% antibiotic, 10-20% anti-inflammatory agent, 20-30% anti-allergic agent, 20-30% vitamin A, 2-6% hyaluronadase, 3-5% carbamide (urea), 2-5% cytokinase, and 10-20% vasoconstrictor. These agents may be combined in a hyper- or hypotonic solution. The composition may also include a vehicle such as a polymer (e.g., methylcellulose, cellulose, polyvinylalcohol, polyethylene glycol, etc.) The agents may be administered in combination or separately. As will be appreciated by one of skill in this art, one or more of the agents may be removed from the pharmaceutical composition as determined by the treating physician. Also as will be appreciated by one of skill in this art, various substitutions may be made for the agents in the pharmaceutical composition. For example, different broad spectrum antibiotics may be used depending on such factors as allergies of the patient, costs, likely organisms, etc. In addition, various anesthetics, anti-inflammatory agents, vasoconstrictors, anti-allergic agent, and cytokinase may be used.

In certain embodiments, the molding contact lenses and the pharmaceutical composition are provided in a kit. The kit may optionally include lubricating eyedrops, cleaning solutions for the contact lenses, a contact lens carrying case, an extra pair of contact lenses, and instructions for wearing the contact lenses and using the pharmaceutical composition.

With all the elements considered above, the mathematical formulae for correcting presbyopia with the present inventive method are as follows:

$$R_f = [332/(332/R_i + D_v)] + R_{(sphere\ and\ cylinder\ of\ visual\ memory)}$$

$$D_f = D_i + D_v = (332/R_i) + D_v + D_{(sphere\ and\ cylinder\ of\ visual\ memory)}$$

Where $R_f$, $R_i$, $D_f$, $D_i$, and $D_v$ are as previously defined. If should be born in mind that the calculations for the molding contact lens prescription can be performed by a computer programmed with the formula described herein.

In patients with presbyopia and who require refractive surgery, it is necessary to induce the changes in the cornea suggested by the mathematical formula of compound myopic astigmatism with a vertical axis (or horizontal or oblique) so that the patient's visual system (including visual memory) begins to accept the new images and together with cerebral accommodation train and educate the patient to change his or her habits for near and far vision.

Once the desired endpoint has been achieved using the inventive system, the use of the molding contact lenses and the pharmaceutical composition is discontinued. The treatment may be repeated if the patient's vision or visual needs change over time. For example, if presbyopia increases, re-treatment may be necessary. Or if the patient changes work habits, re-treatment may be necessary. Aging may also cause changes in vision requiring re-treatment. As already mentioned, the patient guides the treatment to achieve the vision desired. Consequently, based on the information provided by the patient and the results obtained in measuring the refractive power of the cornea, if the patient desires, if far vision is better than near vision, then the radius of curvature of the anterior corneal surface (both in sphere and in cylinder) needs to be steepened. If the patient has better near vision than far vision, the radius of curvature of the anterior corneal surface needs to be flattened. If the image is distorted, a change in astigmatism (cylinder) axis is induced until vision improves.

With each evaluation, the decision is made whether to continue with the same molding contact lens or whether a new contact lens should be used. In addition, the same decision must be made with regard to the pharmaceutical composition being used with the molding contact lenses.

Another important aspect of the inventive method is that it can be used to change the refractive power of the cornea to improve upon the result of any refractive surgery or other technique to correct refractive errors. In patients recently having undergone a refractive surgery, the refractive power of the cornea can be tuned up or improved. As described above, in almost all refractive surgeries there remains a residual refractive error that can be corrected or improved to reach the vision that the patient requires. During the first four weeks after refractive surgery (which is the approximate time it takes for the corneal wound to completely heal), changes in the refractive power of the cornea can be induced. In certain embodiments, the inventive treatment is started 24 hours, 48 hours, 73 hours, or one week post surgery. External pressure on the cornea caused by a molding contact lens can change the radius of curvature of the anterior surface of the cornea to improve the patient's vision and fix or reduce any refractive errors left after the refractive surgery. Since any residual defects in refraction can be corrected using the inventive technique, refractive surgeries are complemented by the inventive technique. In certain circumstances, the inventive technique becomes an obligatory complement to refractive surgery.

In FIG. 2, Sturm's conoid is shown which mathematically speaking shows the circle of less confusion produced by a sphero-cylindrical lens (e.g., the cornea in the human eye), which is the point in which all the light beams cross through. The Sturm's conoid considers the sphero-cylindrical lens as a smooth and uniform surface as if it was made of glass or plastic.

Ophthalmologists continue to refer to the compounded myopic astigmatism as an incorrect solution for the correction of presbyopia because they think there are going to be producing two images at the level of the retina and therefore the patient cannot see well with the myopia and astigmatism that is to be induced. The ophthalmologist and the optometrist also performs the measurements at the base of the two plane of the Sturm's conoid and in the circle of less confusion. However, such an interpretation should be made in a different way which involves one of advantages of the inventive system. The light beams that form any image at the level of the retina can be interpreted for para-axial optics which consists of considering the measurement of a small central zone of the cornea and in the apex or axial-axis, including only the light beams near the central beam, the so-called power axis, and cannot predict aberrations in the images except astigmatism and refractive errors as myopia. The calculations of the para-axial optics are relatively easy to do and can be done by hand, with a calculator, or with a computer. Also, the calculations are performed based on geometric optics, which have the limitation that it does not consider the light as a wave but rather considers the propagation of light as a beam (i.e., a straight line in a uniform medium with a constant refractive index). The method for the calculation of the geometric optics consists of tracing the beams and typically involves using a computer programmed to perform such calculations. The most important, useful, and fundamental theory is that which incorporates optics and physics. Such a theory takes into account the fact that light is a wave. This theory predicts the interference of the wave and the diffraction (when the wave crosses surfaces of different radii, thicknesses, and/or refractive indexes like the cornea, lens, and other elements of the eye). The calculations of the optics using this approach are more difficult. Nevertheless, this approach still does not contemplate the irregularities of the retina and the differences in radius and thickness of each element that intervenes and differences in the refractive indexes in each eye separately. Therefore, this calculation is also not perfect.

Figure 3:
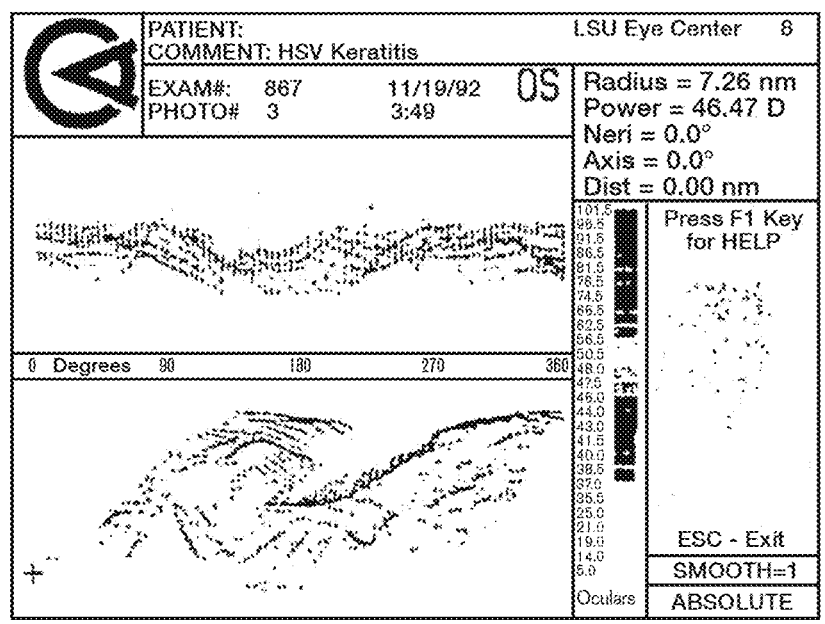
FIG. 3 is a photograph that shows the differences that exist in the thickness and radius of curvature of the anatomical regions of the eye.

With the inventive technique, the disadvantages described above can be minimized or eliminated because this inventive system takes into account the visual memory and the cerebral accommodation of the particular patient, and the point spread function (PSF) in the retina. As is shown in the isometric topography maps in FIG. 3 (Rabinowitz et al., *Color Atlas of Corneal Topography, Interpreting Videokeratography*, Igaku-Shoin Medical Publishers, Inc., p. 65; incorporated herein by reference), both the anterior and posterior surfaces of the cornea have irregular surfaces for which it is only possible to use the circle of less confusion approach to the best nitid possible. The anterior surface of the cornea becomes more uniform through the inventive system. In making the anterior surface of the cornea more uniform and inducing changes in the refractive power of the cornea, the inventive system is guided by the visual needs and visual memory of the patient for both near and far vision.

As described supra, all the surfaces of the cornea are different in their radii of curvatures and thicknesses. The circle of less confusion and the point spread function in the retina is blurrier than it is typically calculated. The reason why certain individuals have not needed eyeglasses or contact lenses before is simply due to the fact that their refractive error is very low, e.g., myopia of 0.690 diopters and astigmatism of 0.712 diopters (actual measurements would be myopia of 0.50 D and astigmatism of 0.75 D). The brain with the visual memory and cerebral accommodation including the optic-cerebral-motor system can compensate for these small refractive defects with the muscles and the areas of the eye that permit the proper focus or accommodation of the defect in refraction.

The circle of less confusion that is found in the retina of the human eye does not correspond to a completely uniform circle and is not spherical in its circumference. In addition, the anatomical irregularities of the cornea produce an infinite number of very small but different focal points that are impossible to calculate. As is appreciated by ophthalmologist and optometrists, this is complicated even further when one realizes that these small irregularities are found in each anatomical structure of the eye.

It should be noted that during a typical LASIK surgery the corneal disk is lifted and the laser beam is applied to produce an ablation. In other surgical techniques that involve cuts or stromal ablations like the LASIK technique, the corneal disk is allowed to slide into the resected stromal space. The inventive technique makes use of stromal sliding. The pharmaceutical composition administered to the eye allows or preferably enhances the stromal sliding, which allows the cornea to steepen or flatten by the pressure exerted by the molding contact lens. Only when the inventive technique is used after a refractive surgery can the stromal sliding be observed. The stromal sliding is produced in all surfaces of the keratectomy where only tenth of microns or microns are needed to the correct the residual refractive defect left by the surgery. The inventive system allows vision to reach the optimum for both eyes, e.g., in the myopic sphere of 0.567 D and in the myopic astigmatism 0.682 D, with an axis of 122.5°.

The corneal disk is displaced toward the periphery to correct more myopia by flattening the radius of curvature of the anterior surface of the cornea or is displaced toward the center of the cornea to improve hyperopia or presbyopia by steepening the radius of curvature of the anterior surface of the cornea (see "Cirugia Refractiva de la Cornea", Instituto Barraquer de America, Bogota, Colombia, 1999, p. 171; incorporated herein by reference), The formula for the stromal sliding is already developed in "Cirugia Refractiva de la Cornea", Instituto Barraquer de America, Bogota, Colombia, 1999, p. 171.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A non-invasive method for treating an ophthalmic condition associated with an error in refraction of the eye, the method comprising steps of:
   providing a contact lens;
   providing eye drops comprising an effective amount of hyaluronidase and collagenase, wherein the collagenase is not matrix metalloproteinase 1 or matrix metalloproteinase 2;
   applying the contact lens to an eye of a patient suffering from the ophthalmic condition; and
   applying the eye drops to the eye of the patient;
   wherein the treatment corrects the patient's vision, and the treatment results in corrected vision for at least 6 months.

2. The method of claim 1, wherein the contact lens is an extended wear contact lens.

3. The method of claim 1, wherein the contact lens is a gas permeable contact lens.

4. The method of claim 1, wherein the contact lens is a molding contact lens.

5. The method of claim 1, wherein the treatment induces a change in the shape of the cornea.

6. The method of claim 1, wherein the treatment induces a change in the physiology and anatomy of the cornea by changing the radius of curvature of the anterior surface of the eye.

7. The method of claim 1, wherein the eye drops further comprise at least one agent selected from the group consisting of enzymes, anesthetics, vitamins, zinc, antibiotics, anti-allergic agents, carbamide, cytokinases, vasoconstrictors, anti-viral agents, anti-fungal agents, anti-inflammatory agents, and lubricants.

8. The method of claim 1, wherein the eye drops further comprise a polymer.

9. The method of claim 8, wherein the polymer is selected from the group consisting of methylcellulose, cellulose, polyvinyl alcohol, and polyethylene glycol.

10. The method of claim 1, wherein the eye drops are hypertonic.

11. The method of claim 1, wherein the eye drops are hypotonic.

12. The method of claim 1, wherein the eye drops comprise about 0.01% to about 10% (weight percent) hyaluronidase, and about 0.01% to about 10% (weight percent) collagenase.

13. The method of claim 1, wherein the treatment results in the correction of up to 3 diopters of refractive error without surgery.

14. The method of claim 1, wherein the treatment results in the correction of up to 4 diopters of refractive error without surgery.

15. The method of claim 1, wherein the treatment results in the correction of up to 5 diopters of refractive error without surgery.

16. The method of claim 1, whereby the treatment results in corrected vision for at least 1 year.

17. The method of claim 1, wherein the ophthalmic condition is a residual refractive error present after a surgical procedure involving the eye.

18. The method of claim 17, wherein the surgical procedure is keratotomy, keratomileusis by a freezing process, automated lamellar keratomileusis, photo-reactive keratomileusis, laser-assisted in situ keratomileusis, later intrastromal keratomileusis, laser epithelial keratomileusis, conductive keratoplasty, or scleral resection.

19. The method of claim 17, wherein the surgical procedure includes cutting corneal or sclera tissue and/or ablating areas of the cornea.

20. The method of claim 1, wherein the ophthalmic condition is a genetic refractive defect.

* * * * *